(12) United States Patent
Shaw (10) Patent No.: US 9,245,093 B2
(45) Date of Patent: Jan. 26, 2016

(54) PILL DISPENSING SYSTEM AND APPARATUS

(71) Applicant: Thomas J Shaw, Frisco, TX (US)

(72) Inventor: Thomas J Shaw, Frisco, TX (US)

( * ) Notice: Subject to any disclaimer, the term of this patent is extended or adjusted under 35 U.S.C. 154(b) by 175 days.

(21) Appl. No.: 13/842,703

(22) Filed: Mar. 15, 2013

(65) Prior Publication Data

US 2014/0277702 A1   Sep. 18, 2014

(51) Int. Cl.
| | | |
|---|---|---|
| *A61J 7/04* | (2006.01) |
| *G06F 19/00* | (2011.01) |
| *G07F 11/00* | (2006.01) |
| *G07F 11/52* | (2006.01) |
| *G07F 17/00* | (2006.01) |
| *A61J 7/00* | (2006.01) |

(52) U.S. Cl.
CPC ........... *G06F 19/3462* (2013.01); *A61J 7/0084* (2013.01); *A61J 7/0481* (2013.01); *G07F 11/005* (2013.01); *G07F 11/52* (2013.01); *G07F 17/0092* (2013.01); *A61J 2200/30* (2013.01)

(58) Field of Classification Search
CPC .... G06F 17/0092; A61J 7/0084; A61J 7/0481
See application file for complete search history.

(56) References Cited

U.S. PATENT DOCUMENTS

| | | |
|---|---|---|
| 3,815,780 A | 6/1974 | Bauer |
| 3,911,856 A | 10/1975 | Ewing |
| 3,985,264 A | 10/1976 | Shaw et al. |
| 3,998,356 A | 12/1976 | Christensen |
| 4,087,020 A | 5/1978 | Krakauer |
| 4,207,992 A | 6/1980 | Brown |
| 4,223,801 A | 9/1980 | Carlson |
| 4,275,384 A | 6/1981 | Hicks et al. |
| 4,360,125 A | 11/1982 | Martindale et al. |
| 4,473,884 A | 9/1984 | Behl |
| 4,572,403 A | 2/1986 | Benaroya |
| 4,573,606 A * | 3/1986 | Lewis et al. ................. 221/2 |
| 4,674,651 A | 6/1987 | Scidmore et al. |
| 4,695,954 A | 9/1987 | Rose et al. |
| 4,809,877 A | 3/1989 | Albright |
| 4,811,764 A | 3/1989 | McLaughlin |
| 4,838,453 A | 6/1989 | Luckstead |
| 4,953,745 A | 9/1990 | Rowlett, Jr. |
| 5,077,462 A | 12/1991 | Newell et al. |
| 5,176,285 A | 1/1993 | Shaw |
| 5,472,113 A * | 12/1995 | Shaw ........................ 221/7 |
| 5,609,268 A | 3/1997 | Shaw |
| 6,330,957 B1 * | 12/2001 | Bell-Greenstreet ........ 221/3 |
| 6,471,087 B1 * | 10/2002 | Shusterman ............... 221/2 |

(Continued)

FOREIGN PATENT DOCUMENTS

GB          2178733         2/1987

*Primary Examiner* — Timothy Waggoner
(74) *Attorney, Agent, or Firm* — Ross Barnes LLP; Monty L. Ross; Robin L. Barnes (57) ABSTRACT

An automatic pill dispensing system and apparatus are disclosed that include a plurality of pill storage cartridges, a control system configured to dispense pills at predetermined times and intervals. The dispensed medications, dosage times, patient compliance information, other prescription information are programmed or available to a caregiver, physician, other medical personnel or pharmacist either directly or remotely by a caregiver through an interface that is not accessible to the patient. The apparatus signals the patient at appropriate times and pills are dispensed when the patient depresses a single dispense button to discharge the prescribed medications into a tray.

8 Claims, 5 Drawing Sheets

(56) References Cited

U.S. PATENT DOCUMENTS

| | | |
|---|---|---|
| 6,510,962 B1 | 1/2003 | Lim |
| 7,137,528 B1 * | 11/2006 | Yates et al. ............... 221/82 |
| 8,600,548 B2 * | 12/2013 | Bossi et al. ............... 700/240 |
| 8,670,865 B2 * | 3/2014 | Coe ............... 700/243 |
| 8,874,260 B2 * | 10/2014 | Saltsov ............... 700/244 |
| 2003/0183642 A1 | 10/2003 | Kempker, Sr. |
| 2008/0283542 A1 | 11/2008 | Lanka et al. |
| 2011/0125315 A1 | 5/2011 | Handfield et al. |

* cited by examiner

PILL DISPENSING SYSTEM AND APPARATUS

BACKGROUND OF THE INVENTION

1. Field of the Invention

This invention relates to a pill dispensing system and apparatus, and more particularly to an automatic pill dispensing device for dispensing a plurality of pills at selected times over a predetermined period of time. The system can include remote notification and remote access capabilities.

2. Description of Related Art

The use of daily medication is increasingly common today, particularly among the elderly. While some elderly patients are in nursing homes or are being attended by health care professionals, many others care for themselves. Those individuals must be careful to take the proper dosage of the correct medication at the appropriate time each day. This can be a difficult task for patients suffering memory loss and for those taking several different medications at various times throughout the day. Some patents can have trouble remembering and dealing with several different medications requiring different doses at different times and frequencies, and mistakes can lead to potential life threatening circumstances such as overdosing, under dosing or improper dosage combinations. Furthermore, arthritis or other physical impairments can make it difficult for some elderly to open the various pharmaceutical pill containers with the child safety lock mechanisms. The resulting loss of peace of mind and anxiety to both the elderly and their families and friends is tremendous.

Numerous devices have been developed for automatically dispensing pills and medication at timed intervals. These devices range from simple machines, in which a timer controls rotation of a pill dispenser causing the dispensing of a pill at a pre-programmed time regardless of any action or confirmation of the patient, to complex machines that are controlled by a microprocessor and have the ability to remotely notify a physician or caregiver if the patient fails to take one of the dispensed medications.

The known prior art pill dispensing devices are not remotely accessible by physicians and caregivers, so that the physicians and caregivers can view a real time report on the dispenser's operability and prescription compliance by the patient, and assess how soon the dispenser will need to be refilled. Known prior art pill dispensing devices are not capable of remotely notifying the patient when it is time to take the next dosage. Several prior art dispensing devices have an audible alarm that sounds when the dispenser is ready to dispense, but this is not satisfactory for the many elderly who are hearing impaired. If the dispenser is in the kitchen and the patient is in the living room or bedroom, the patient may not hear the alarm on the dispenser, especially if there is other ambient noise, such as a television or radio. Some prior art devices require the patient to wear a vibrating device around the neck or wrist that vibrates when the dispenser is ready to dispense, but this separate device can be misplaced or the battery may go dead. Other prior art dispensing devices contact another machine, such as a computer, to remotely notify the patient. However, there is a risk that the separate machine may be turned off or be otherwise non-operational causing the patient to miss a critical dose.

The known prior art devices that disclose the dispensing of multiple medications through the use of multiple dispensing wheels or cassettes do not provide for linking the wheels or cassettes if the same medication is loaded into multiple wheels. For example, if the prior art device has six dispensing wheels but the patient is only taking five different medications, then the sixth wheel would be left empty in the prior art devices. However, if the most frequently taken medication was also loaded into what would be an otherwise empty wheel and the dispenser was programmable to link the two wheels with same medication, then the dispenser could first empty the original wheel containing the medication and then begin to empty the second wheel, effectively doubling the interval for refilling the machine.

It is therefore desirable to have a simple and reliable automatic pill dispensing system and apparatus capable not only of dispensing a plurality of pill prescriptions at timed intervals and in proper dosages from a plurality of pill compartments but also of notifying the patient, both proximally and remotely, when a pill is ready to be dispensed. It is also desirable for the dispenser to allow an outside caregiver or physician to access the machine remotely to ensure the patient is taking the pills in compliance with the prescription schedule, and for the dispenser to remotely contact the physician or caregiver if a critical dose is missed or if one of the pill compartments needs to be refilled. It is also desirable for an automatic pill dispensing system and apparatus to be easy to program and load, and to allow linking of more than one of the cartridges containing the same medication so that the time between refills is extended.

SUMMARY OF THE INVENTION

The present invention embodies a pill dispensing system and apparatus capable of dispensing a plurality of medications at proper intervals and in the proper doses, which incorporates novel electronic and mechanical technology. The present invention comprises a plurality of circular cartridges that are supported by a solid axle running through the center of each cartridge. The present invention also comprises remote access capability in which software acts as an Internet appliance allowing caregivers and physicians to view the status of the dispenser using a web browser or other application software installed on a cell phone, tablet or other device. The present invention provides remote notifications in which the patient is alerted that medication is ready to dispense by an audio alert as well as other systems such as home automation, lighting controllers, personal computers or other audio visual equipment. The present invention also provides notification to the patient at the appropriate time for the patient to take a medicine if away from the dispenser on a vacation. Moreover, the dispenser can link more than one of the cartridges, thereby increasing the time the dispenser can operate before it needs to be refilled.

In a preferred embodiment, a pill dispenser for dispensing pills from selected ones of a plurality of cartridges according to a predetermined prescription schedule comprises a housing adapted for holding a plurality of cartridges, a drive means for rotating the cartridges, a motion control unit for controlling the drive means and a main control unit for operating the electronic and communication operations of the dispenser. The housing further comprises a pill dispensing tray to receive the pills as they are dispensed, a dispense button and an LCD touch screen display.

The main control unit, in connection with a real time clock, communicates to the motion control unit when it is time to dispense a pill from one or more of the cartridges according to the predetermined prescription schedule. The motion control unit communicates with the drive means, which rotates the cartridge from which the pill is to be dispensed to a specific position. The cartridges have pill compartments about their periphery, with each compartment having an open end at its periphery. The open end of one pill compartment at a time is selectively positionable by rotation of the cartridge to a position in communication with a dispense bar, which closes the open end. This defines a dispensing position. Once the desired cartridge or cartridges are in the dispensing position, the dispenser provides an audio and other remote notification alerts to the patient to signal that it is time to dispense medication. The patient then depresses the dispense button, which causes the dispense bar to pivot downward and the sweeping wire to move through the pill compartment towards the open end, causing the pill to fall into the dispense tray.

The plurality of cartridges are preferably mounted in the housing and supported by a solid axle that runs through the center of all cartridges. The individual pill compartments have rigid side walls and are closed by a wall that encircles the cartridge. When the cartridge is disposed in the dispenser, the wall does not rotate and has an opening which is in communication with the dispensing bar. The cartridges are individually rotatable to successive dispensing positions wherein successive compartments become open as they become aligned with the opening in the wall. The wall is preferably provided on a removable cover member that cooperates with the rotatable portion of the cartridge to enclose pills loaded therein by the patient, a pharmacist or care giver. The removable cover is held in place by a spring clip. The dispense bar in its closed position closes the opening and prevents the pills from exiting the pill compartment until the patient depresses the dispense button. In a preferred embodiment, the top of the dispense bar is covered a thin piece of a non-rigid, compressible material, such as the hook portion of a hook-and-loop fastener. This material keeps the pill elevated as it crosses the dispense bar, which prevents pills from being crushed, jamming the machine, or falling out of the compartment as the end of the rigid side wall sweeps along the material on top of the dispense bar.

The drive means preferably comprises a stepper motor driver, a stepper motor and individually engageable clutch means that cause the cartridges to rotate in response to a signal from the motion control unit. The stepper motor turns the shaft, and the clutch driver engages the clutch on the complementary gear of the specific cartridge that is to be moved into the dispensing position. The cartridge is turned until the next pill compartment is in the pill dispensing position. A servo motor can be used instead of a stepper motor, but a stepper motor is preferred so that the precise position of the cartridge is known by motion control unit at all times due to the motion control unit being able to count the steps the motor has taken. The precise position of the cartridges is also verified by using a sensing means associated with each cartridge wherein the sensing means provides signals to the motion control unit. The sensing means preferably comprises infrared proximity sensors mounted in a fixed position in the housing wherein the receiver and transmitter are placed less than a quarter-inch apart. Individual slot openings corresponding to each pill compartment are located toward the outer edge of the cartridge, which passes between the infrared receiver and transmitter. A slot is used in the preferred embodiment rather than a circular hole because the slot allows for more precise placement of the cartridge. The wheel sensors are monitored as the wheels are moving, and the logic in the motion control unit tabulates the number of steps the stepper motor has turned between the sensing of slot positions in the cartridge. The home position of the cartridge is desirably the same width as a pill compartment at the periphery, but it is not intended to contain a pill. There is no slot opening corresponding to the home position. When the stepper has turned the number of steps so that the sensing means should be registering a slot for the next dispensing position but no slot is sensed, the motion control unit recognizes this as the home position.

The main control unit and motion control unit of the dispenser is are microprocessor-based systems. The main control unit is programmable to receive, store and process a predetermined prescription schedule. The main control unit, when used in conjunction with a real time clock, is capable of determining the appropriate time for dispensing pills. The motion control unit and the main control unit can be discrete devices or can be integrated into a single device. The main control unit is configured to support a graphical user interface with a LCD touch display along with several possible channels of remote communications for communication outside the dispenser. The LCD touch display is the preferred user input device. The main control unit also comprises a communication link with the motion control unit to command the movement of the cartridges and the dispense bar.

The dispenser has the ability to communicate remotely, which allows information to be accessed and transferred from a remote location. Additionally, the dispenser can also communicate optionally with other systems such as home automation, lighting controllers, PCs or other audio/visual equipment with communication ports to blink lights, generate audio alerts, etc., in case the patient is out of audio range of the dispenser when the cartridge is in a dispensing position and a dispense alert is sounded.

The dispenser is capable of generating several different notifications that it can send through its remote communications ability to physicians and caregivers. Such notifications can optionally include whether the patient has missed a critical dose, how much longer the dispenser can operated before needing to be refilled, and if the dispenser is having any technical difficulties. The patient can also set the dispenser to vacation mode in which the dispenser will not dispense any medication, but will notify the patient through its remote notification capabilities at the appropriate time to take a medication. The dispenser also maintains a log of all activity through the non-volatile memory of the main control unit, wherein the log includes patient and caregiver information, medication schedules, actual medication dispenses, missed dispenses, loss of AC power, error conditions, etc. The main control unit allows for flexible dispense windows, which allows the caregiver to set the length of time in which the patient must depress the dispense button after the cartridge is moved into a dispense position and the audio alert has sounded. The main control unit of the dispenser also desirably provides for medication linking in which the same medication can be placed into more than one cartridge if the patient requires fewer than six medications, which increases the time before a refill is required.

The novel features and construction of the present invention will be understood more fully from the following description when read in connection with the accompanying drawings.

BRIEF DESCRIPTION OF THE DRAWINGS

The improved process of the invention is further described and explained in relation to the following figures of the drawings wherein.

Like reference numerals are used to describe like parts in all figures of the drawings.

DESCRIPTION OF THE PREFERRED EMBODIMENTS

Figure 1:
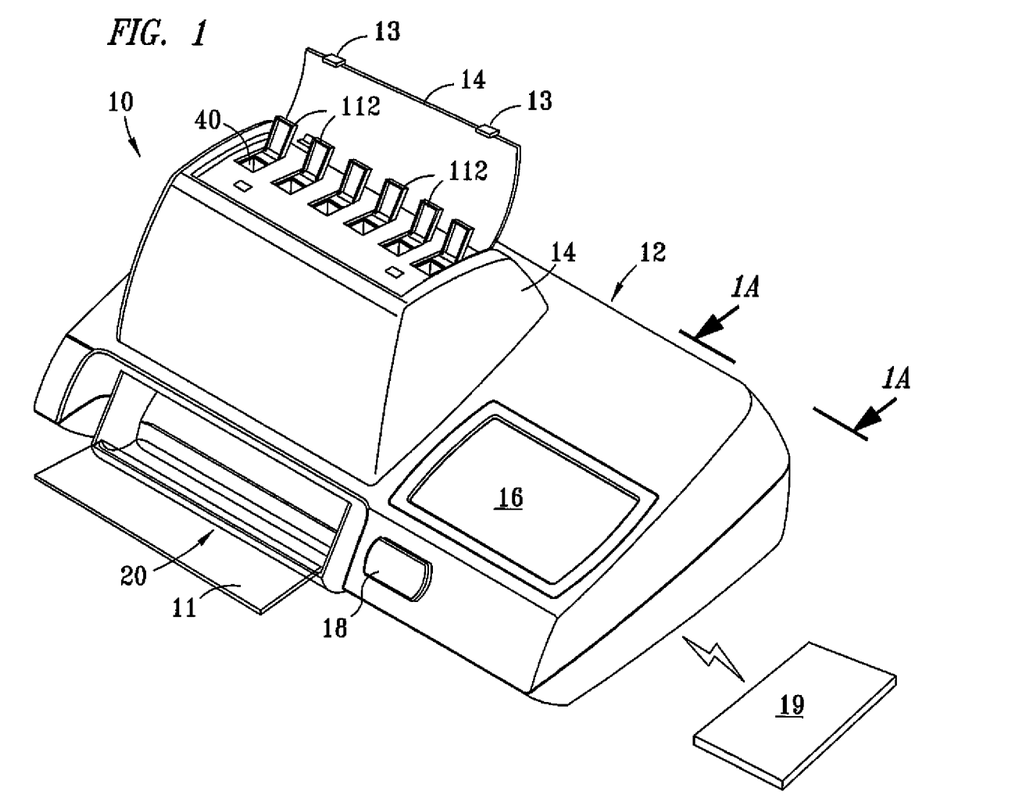
FIG. 1 is a perspective view of a pill dispensing apparatus made in accordance with the preferred embodiment of the present invention.

Referring to FIG. 1, a preferred embodiment of an automatic pill dispensing system and apparatus is shown. Pill dispensing apparatus 10 includes a housing 12, which houses microprocessor components and mechanical components discussed below. Housing 12 comprises a cover 14, an LCD display 16, a dispense button 18, a dispense tray 20, and a dispense door 11. Housing 12 is accessible by cover 14, which is kept closed by the use of a mechanical latch 13 to deter access by the patient. Display 16 is situated on housing 12 in a position such that it is easy to view and touch by a patient or caregiver located in front of pill dispensing apparatus 10. Similarly, dispense button 18 is also situated in an easy to reach location on a front of housing 12. Also illustrated in FIG. 1 is a smart device 19, such as a smartphone or tablet computer, which can communicate with pill dispensing apparatus 10 by wifi, Bluetooth, or other wireless technology.

Accessible through cover 14 are cartridge doors 112 and fill openings 40. To load pills in a cartridge 32, a caregiver accesses cartridge 32 through cover 14. The caregiver then opens the cartridge door 112 corresponding to the appropriate cartridge 32 and inserts a pill through fill opening 40.

Figure 1A:
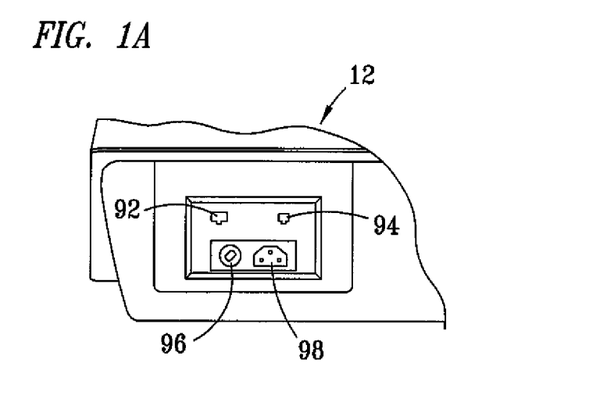
FIG. 1A is a partial elevation view taken along line 1A-1A of FIG. 1.

FIG. 1A illustrates examples of ports that can be provided on pill dispensing apparatus 10. The ports are preferably positioned on a back part of housing 12. In FIG. 1A, housing 12 comprises an Ethernet port 92, a telephone jack 94, a voltage selector 96, and a power jack 98. Voltage selector 96 is desirably configured at the factory to select 110v or 220v based on anticipated local availability.

Figure 2:
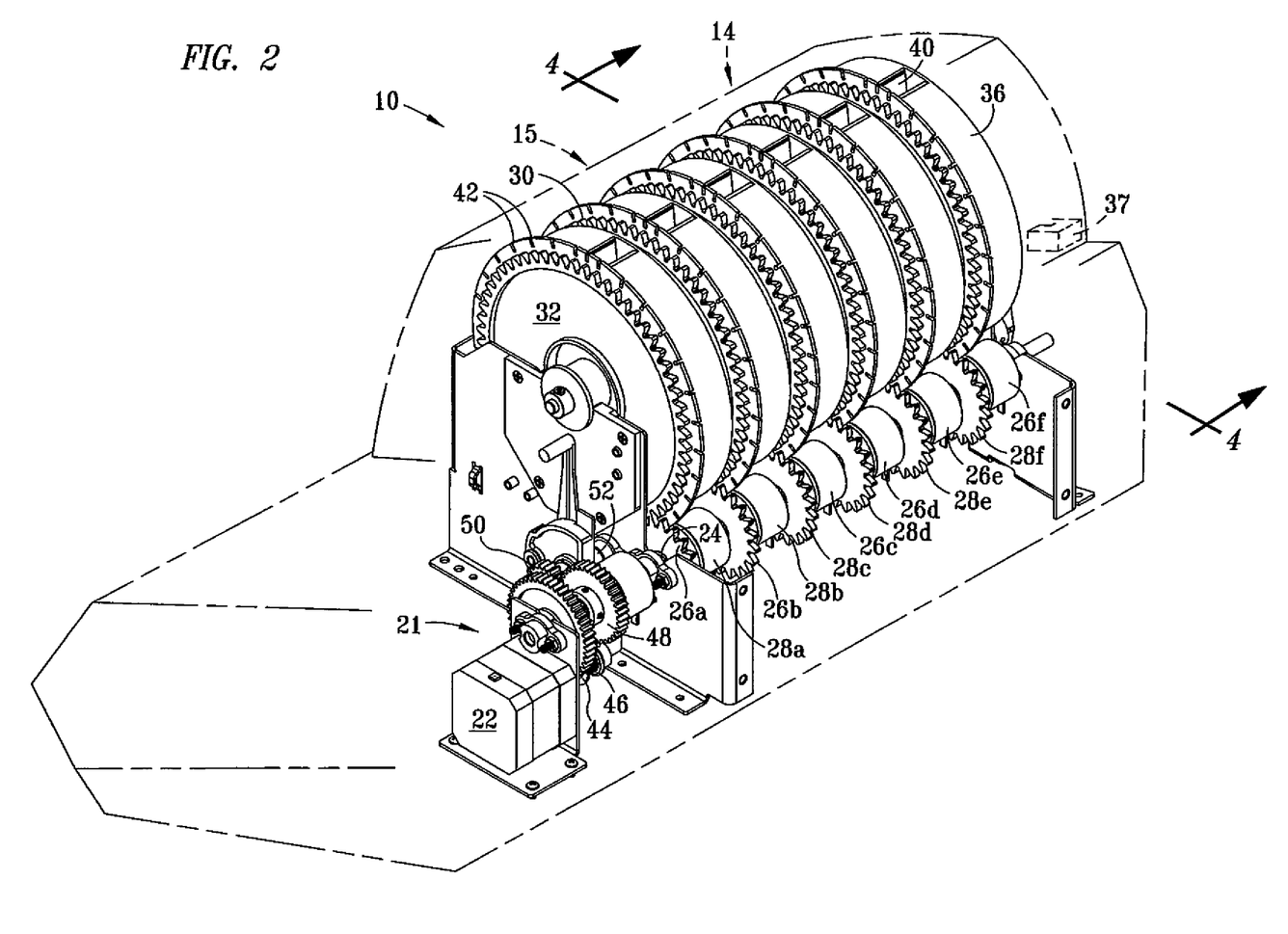
FIG. 2 is a perspective view of the mechanical components of the pill dispensing apparatus of FIG. 1.

Referring to FIG. 2, mechanical components 21 of pill dispensing apparatus 10 are shown. Mechanical components 21 comprise electrical motor 22 and a plurality of gears, shafts and clutches, which will be discussed in greater detail in turn. In the preferred embodiment, electrical motor 22 is a stepper motor. Electrical motor 22 directly rotates a horizontally disposed primary shaft 44, which is coupled to primary gear 46, and the rotation of primary shaft 44 causes rotation of primary gear 46. The rotation of primary gear 46 causes secondary gear 48 to also rotate. Secondary gear 48 is attached to secondary shaft 24, such that the rotation of secondary gear 48 causes secondary shaft 24 to rotate. Secondary shaft 24 preferably runs the entire length of pill dispensing portion 15 of pill dispensing apparatus 10, and shaft 24 preferably includes electromechanical clutches 26a-f, which are coupled with cartridge drive gears 28a-f. Each of cartridge drive gears 28a-f is attached to one of clutches 26a-f, and clutches 26a-f prevent shaft 24 from rotating cartridge drive gears 28a-f unless the corresponding clutch 26a-f is engaged.

Each of cartridge drive gears 28a-f rotates one of the plurality of pill dispensing cartridges 32 by engaging cartridge gear teeth 30. In a preferred embodiment, pill dispensing apparatus 10 houses six cartridges 32, although other numbers of cartridges 32 can be used. Cartridges 32 rotate around axle 34. A cartridge cover 38 is held in place by spacer 36. The preferred embodiment of cartridge 32, cartridge cover 38, axle 34 and spacers 36 are discussed in greater detail in regard to FIG. 3. Cartridge cover 38 has a fill opening 40 located at an upward location. Fill opening 40 allows medicine to be loaded into cartridge 32. Slits 42 on the periphery of cartridge 32 are used in conjunction with infrared sensors 37, which will be discussed in greater detail in regards to FIG. 4.

The rotation of primary shaft 44 coming out of motor 22 in conjunction with primary gear 46 and secondary gear 48 turns gear 50. Gear 50 is coupled to horizontally disposed shaft 52 through an electromechanical clutch. When the clutch engages, the rotation of gear 50 causes shaft 52 to rotate. Shaft 52 is attached to a plurality of pivoting dispense bars (not shown), and there is one dispense bar for each cartridge 32. The pivoting dispense bars are discussed in conjunction with FIG. 4.

For example, when it is time to dispense a pill from cartridge 32 corresponding to clutch 26e and gear 28e, a patient depresses dispense button 18 (shown in FIG. 1). Motor 22 then rotates shaft 44, which in turn rotates shaft 24 through the use of complimentary gears 46 and 48. Clutch 26e engages and rotates gear 28e, which in turn rotates cartridge 32 through cartridge gear teeth 30. Cartridge cover 38 remains stationary as cartridge 32 rotates about axle 34. Stepper motor 22 turns only the certain number of steps required to advance cartridge 32 to the next successive dispensing position. At this time, clutch engages gear 50, which causes rotation of shaft 52. The rotation of shaft 52 causes the dispense bar (not shown) in conjunction with cartridge 32 to pivot downward, thus allowing a pill to fall into dispense tray 20 (shown in FIG. 1). Motor 22 then reverses direction causing in turn shaft 52 to rotate in the opposite direction, which in turn pivots the dispense bar upwards. The patient then removes the pill from dispense tray 20. A tension spring (not shown) is preferably used to bias the dispense bar in an upward (closed) orientation when the clutch is not engaged.

Figure 3:
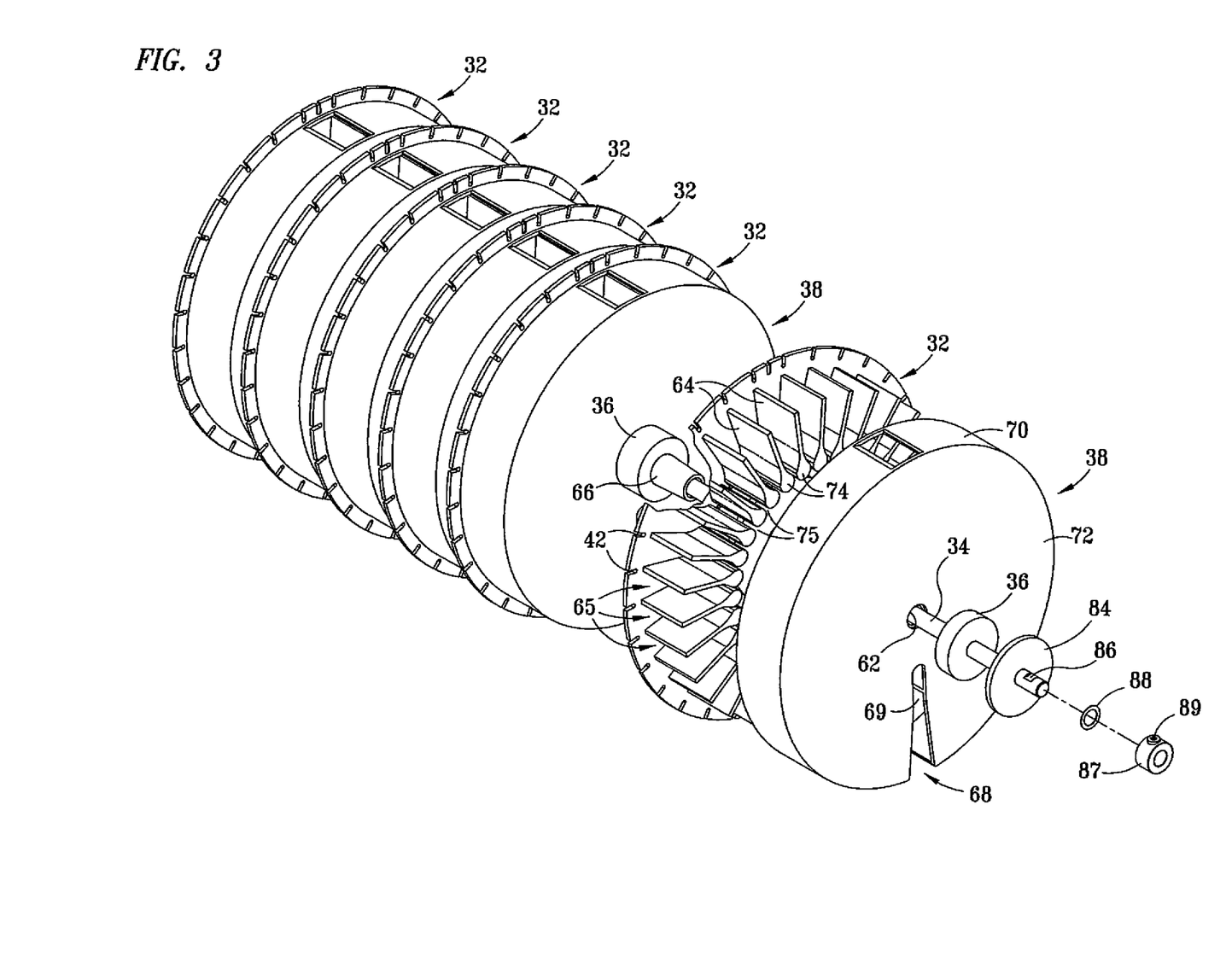
FIG. 3 is an exploded perspective view of one of the plurality of cartridges and cartridge covers for use in the pill dispensing apparatus of FIG. 1.

Referring to FIG. 3, an exploded view of one cartridge 32 and cover 38 is shown. Cartridge 32 is circular in shape and comprises a plurality of pill storage compartments 65 disposed around the periphery of cartridge 32. Pill storage compartments 65 are formed by the location of radially extended adjacently oriented fins 64 that extend from a point approximately halfway along the radius of cartridge 32 to a point almost at the periphery of cartridge 32. Fins 64 further comprise flared out sections 74 located where fins 64 originate. Adjacent flared out sections 74 do not abut and are spaced apart to leave small gap 75 between them such that sweeping wire 84 (shown in FIG. 4) can travel through. However, flared out sections 74 are spaced close enough together to retain pills in pill storage compartments 65. In the preferred embodiment, cartridge 32 comprises 28 pill storage compartments 65, which allows pill dispensing apparatus 10 to operate for one week without needing to be refilled with pills that are to be taken four times a day.

Cartridge cover 38 has a flat face 72 from which cylindrically shaped wall 70 projects at right angles. Cartridge cover 38 is sized such that wall 70 has a slightly larger diameter than the distance between the tips of diametrically opposed fins 64 of cartridge 32. Thus, wall 70 of cartridge cover 38 effectively closes pill storage compartments 65 when cartridge cover 38 is connected with cartridge 32. Cartridge cover 38 has hole 62 in the middle of flat face 72 through which axle 34 protrudes. Cartridge 32 spins freely about axle 34 when attached to cartridge cover 38, and cartridge cover 38 remains stationary when placed inside pill dispensing apparatus 10.

Wall 70 is not a complete cylinder, and flat face 72 is not a complete circle. Flat face 72 has face opening 69, and wall 70 has wall opening 68, which is the same width as pill storage compartments 65 at pill storage compartments' 65 widest point. Face opening 69 and wall opening 68 are correspondingly sized and adjacent to each other. Openings 68 and 69 are opposite fill opening 40 (discussed in regards to FIG. 2). When cartridge 32 and cartridge cover 38 are placed in pill dispensing apparatus 10, openings 68 and 69 face downward and are in alignment with dispense bar 80 (discussed in greater detail in regard to FIG. 4). Fill opening 40 faces upward so that it can be conveniently accessed by a caregiver. Because cartridge cover 38 is stationary, including wall opening 68, and pill storage compartments 65 move relative to cartridge cover 38 as cartridge 32 is rotated, successive pill storage compartments 65 will move into a dispensing position, which is defined as when a pill storage compartment 65 is inline with wall opening 68. When cartridge cover 38 is attached to cartridge 32, slits 42 still extend beyond wall 70, which allows slits 42 to be used in conjunction with the infrared sensors.

Cartridge cover 38 is held against cartridge 32 by spacer 82. After the spacer 82 corresponding to the last cartridge 38, primary washer 84 is placed around axle 34. Adjacent primary washer 84 is secondary washer 88. Lock collar 87 is positioned at an end of axle 34 to prevent other components from slipping off axle 34. Lock collar 87 preferably includes tightening bolt 89, which is configured to engage notch 84 defined in axle 34.

In use, either the patient or the caregiver places one pill in each pill storage compartment 65 of cartridge 32 through fill opening 40. However, if the patient is to take two of the same pills at once, then two pills are loaded into each pill storage compartment 65, which are large enough in the preferred embodiment to hold up to two pills the size of large vitamin-E capsules. After a pills is placed in pill storage compartments 65, cartridge 32 is rotated so that the next pill storage compartment 65 is accessible through fill opening 40.

Figure 4:
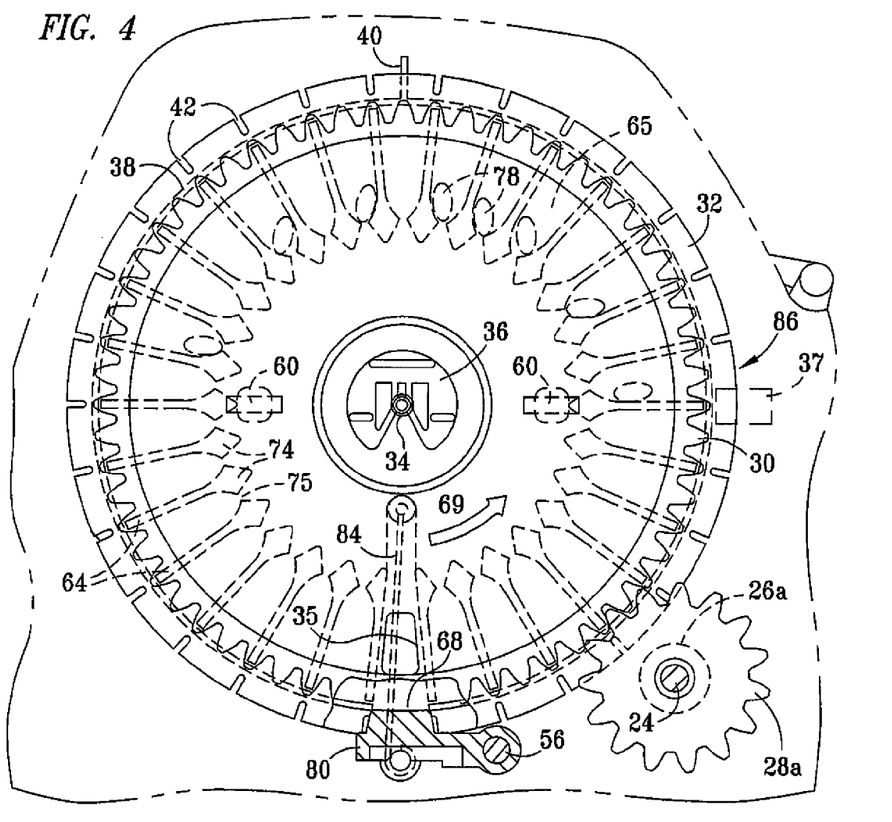
FIG. 4 is an enlarged cross-sectional elevation, partially broken away, view taken along line 4-4 of FIG. 2.
Figure 5:
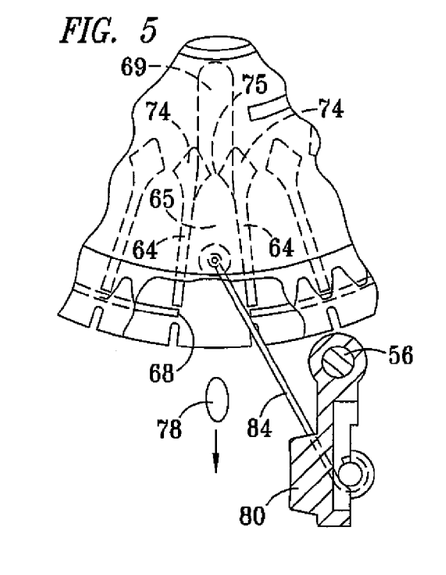
FIG. 5 is detailed view of the lower half of the cartridge shown in FIG. 4.

Referring to FIG. 4, one of the plurality of cartridges 32 and cartridge covers 38 is shown as placed in pill dispensing apparatus 10. The orientation of cartridge cover 38 is such that fill opening 40 is facing upward and wall opening 68 is facing downwards. Washer 36, which fits around axle 34, is keeping cartridge cover 38 in contact with cartridge 32. Pills 78 are located in pill storage compartments 65 and are resting against either fins 64 or flared out sections 74 depending on the positioning of the particular storage compartment 65 in relation to cartridge's 32 rotation. Shaft 24, clutch 26a and gear 28a are shown and were discussed in regards to FIG. 2. As gear 28a rotates, cartridge 32 rotates because gear 28a is coupled with cartridge gear teeth 30 when cartridge 32 is in place inside pill dispensing apparatus 10.

Dispense bar 80 is shown in solid lines in its closed horizontal position and in broken lines in its open vertical position. When dispense bar 80 is in its closed position, it closes wall opening 68 of cartridge cover 38, which in turn is closing pill storage compartment 65 that is currently in a pill dispensing position. In this position, pill 78 are on top of closed dispense bar 80. As shaft 56 rotates a quarter turn counter-clockwise (as discussed in regards to FIG. 2), dispense bar 80 is pivoted downwards, and as shaft 56 rotates back a quarter turn clockwise, dispense bar 80 is pivoted upwards back to its closed position. When dispense bar 80 pivots to its open position, the pill storage compartment 65, which is in a pill dispensing position, becomes open and pill 78 falls into dispense tray 20 (not shown), which is located beneath dispense bar 80.

However, because some types of pills may be sticky or tacky, such as gelatin covered pills, sweeping wire 84 is used to dislodge pills as dispense bar 80 pivots from the closed position to the open position. Sweeping wire 84 is affixed to dispense bar 80, and as dispense bar 80 pivots downward, it pulls sweeping wire 84 through pill storage compartment 65. Sweeping wire 84 has an inverted L-shape. Face opening 69 in cartridge cover 38 extends from above fins 64 all the way to the edge of cartridge cover 38. The vertical component of sweeping wire 84 remains outside cartridge cover 38, while the horizontal component of sweeping wire 84 extends through face opening 69 in cartridge cover 38 and does not interfere with the rotation of cartridge 32 because the horizontal component is located above the upward most sections of fins 64. The horizontal component of sweeping wire 84 is the piece that is pulled through pill storage compartment 65, and it enters pill storage compartment 65 by passing through small gap 75 between flared sections 74 of fins 64. The need for sweeping wire 84 to enter pill storage compartment 65 is why small gap 75 exists.

Slits 42 are evenly spaced around the periphery of cartridge 32, and each slit 42 corresponds to a particular pill storage compartment 65. Infrared sensor 37 comprises both an emitter and receiver and is used conjunction with slits 42 to verify the precise rotational position of cartridge 32. The emitter and receiver of infrared sensor 37 are spaced approximately one-quarter inch apart, and the periphery of cartridge 32, including slits 42, is located between the emitter and receiver. The emitter emits a beam that is to be received by the receiver. However, the periphery of cartridge 32 blocks the beam as cartridge 32 rotates until one of slits 42 passes between the emitter and receiver. At that time, the beam is not blocked and cartridge 32 is in a pill dispensing position. Slits 42 are used rather than circular holes because slits 42 are narrower which makes the positioning of cartridge 32 more precise. In the preferred embodiment where motor 22 (shown in FIG. 2) is a stepper motor, infrared sensor 37 and slits 42 are only used to verify that cartridge 32 is in a pill dispensing positioning because the position of cartridge 32 is known by counting the steps the motor has taken. However, if motor 22 is instead a servo motor, then infrared sensors 37 can be used as the sole way to determine the position of cartridge 32.

Slits 42 are evenly spaced around the periphery of cartridge 32 except at location 86 where no slit is present. Location 86 corresponds to the home position of cartridge 32. When stepper motor 22 has turned the number of steps to put cartridge 32 in the next pill dispensing position but infrared sensor 37 is not registering a slit 42 because location 86 is in line with infrared sensor 37, then cartridge 32 is in its home position. One of pill storage compartments 65 has hole 35, and is not intended to actually store any pills 78. This compartment is in the dispense position when location 86 is in line with infrared sensor 37, so this compartment is in the dispense position when cartridge 32 is at its home position. When cartridge 32 is loaded into the dispenser, motor 22 rotates cartridge 32 until it is in its home position.

The operation of pill dispensing apparatus 10 is controlled through its microprocessor components. Pill dispensing apparatus 10 has a main control unit responsible for operating the electronic and communication operations, and a motion control unit responsible for controlling mechanical components 21 (as discussed above in reference to FIG. 2). The main control unit is programmable to receive, store and process a predetermined prescription schedule. The main control unit, when used in conjunction with a real time clock, is capable of determining the appropriate time for dispensing pills and controlling the pill dispensing apparatus at the appropriate pill dispensing times via a communication link with the motion control unit to command the movement of the cartridges, the dispense drawer and the dispense bar.

After the cartridges are loaded with pills, pill dispensing apparatus 10 must be programmed so that it will be able to dispense the pills from each cartridge at the appropriate time. Information regarding the prescription and the frequency at which the pills should be dispensed is entered either manually through a graphical user interface with a LCD touch display or through the use of a portable memory device capable of storage and a reader to retrieve the information off of the portable memory device. The portable memory device can be a function of the remote access device as described earlier. The LCD touch display is the preferred user input device. The LCD screen allows the caregiver to select a loading option, wherein the caregiver will enter the name of the prescription, any special information such as take with food, and the frequency prescription. From this information, the main control unit calculates the prescription dispensing schedule for that particular cartridge. The main control unit also communicates with a portable memory device. In a preferred embodiment, prescription information, including prescription name, special instructions and frequency, is loaded onto a portable memory device by the pharmacist. The predetermined prescription schedule is then transferred from the smart card to the main control unit, which prevents the information from having to be manually entered via the LCD display, saving time and reducing the possibility of data entry errors.

Once the pill dispensing apparatus is ready to dispense a pill, the patient must depress the dispense button within a set period of time known as a dispense window. The pill dispensing apparatus desirably has a default dispense window of one hour, meaning that a patient must depress the dispense button to take the pill within one hour of being notified that a pill is ready to be dispensed. However, the pill dispensing apparatus allows for flexible dispense windows because some pills must be taken at very specific times and a one hour dispense window would be too long. While entering the prescription information, the pill dispensing apparatus prompts the caregiver to enter the desired length of the dispense window for that particular medication. If none is entered, the default setting of one hour will be used.

Figure 6:
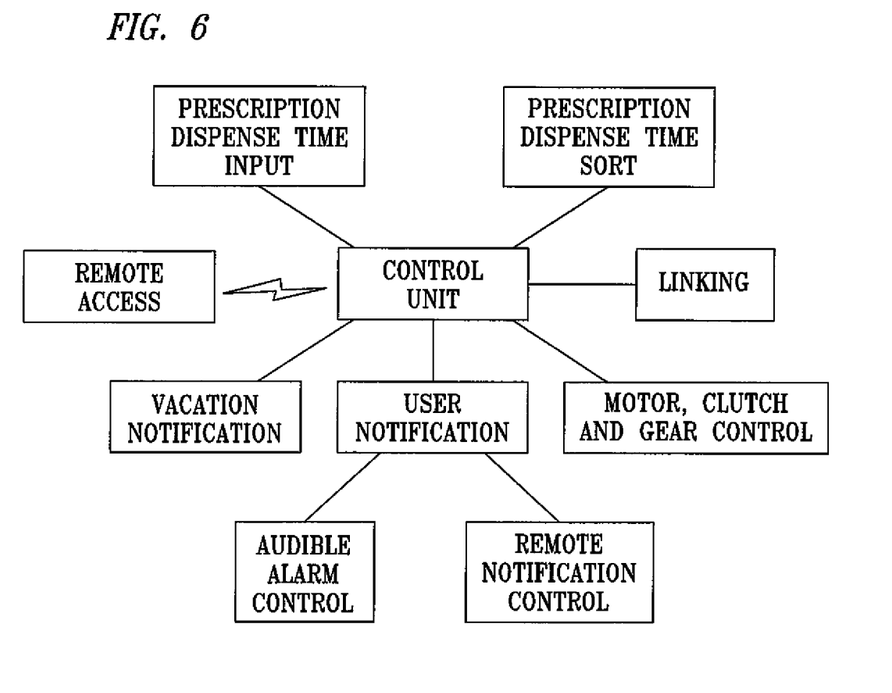
FIG. 6 is a block schematic of the functions performed by the control unit of the pill dispensing apparatus.

Referring to FIG. 6, the main control unit, or control unit, of the dispenser allows for prescription dispense time input through either manual programming or through the use of the portable memory device. The control unit is further capable of sorting the prescription dispense times to calculate the prescription dispense time schedule. The control unit is also able to send control signals to control the motor, clutch and gears of the drive means through control of the motion control unit.

The main control unit of the dispenser also allows for medication linking between different cartridges that are loaded with the same medication. In the preferred embodiment, the pill dispensing apparatus houses six cartridges. However, many patients may not be taking six regular medications. In these instances, the medication taken most frequently can be placed into more than one cartridge and the cartridges can be linked by the main control unit, meaning that the pill dispensing apparatus will treat the two cartridges as effectively just one cartridge. For example, if the same medication is loaded into cartridge one and cartridge two, the pill dispensing apparatus will dispense all the medication from cartridge one and then begin dispensing the medication from cartridge two, which would effectively double the time between refills as compared to if the medication was just in cartridge one. The main control unit calculates when cartridge one will be empty because the number of pill storage compartments is known.

The pill dispensing apparatus is configured for remote access, which allows information to be accessed and transferred from a location not in the proximity of the machine. The pill dispensing apparatus can communicate with either a human through a web browser or another device through a connection directly to the dispenser or over the internet. For human communication the software of the main control unit is structured to act as an internet appliance, which allows caregivers and other authorized personnel to view the status of the dispenser using a web browser from a computer connected to the internet. The main control unit can also be tied into a device that monitors and queries the machine and can track data on an exception basis, like when a the pill dispensing apparatus experiences a mechanical or electrical failure or if the patient misses a dose.

When the main control unit determines that it is time to dispense a pill from a particular cartridge or cartridges and the mechanical components have rotated the particular cartridge to the next successive dispensing position, the main control unit activates an audio alert to notify the patient that a pill dispensing window has begun. Additionally, the patient can be notified remotely because the pill dispensing apparatus has built-in remote communication capabilities that can also communicate to other systems such as home automation, lighting controllers, PCs, cell phones, tablets, or other audio/visual equipment with communication ports to blink lights, generate audio alerts, etc. This remote notification capability does not restrict the patient to be in audio range of the dispenser when the cartridge is in a dispensing position and a dispense alert is sounded, which allows the patient more freedom and helps ensure better compliance by eliminating missed dosages caused by the patient failing to hear the audio alert. The remote communications use both wired (modem/telephone line, Ethernet, etc.) and wireless (wifi, wireless Ethernet, Bluetooth, Zigbee, etc.) links as the low level connections to a larger network such as the Internet or other private networks. Because the remote communication capabilities are built into the pill dispensing apparatus, it does not rely on other devices, which may be turned off or otherwise nonfunctional.

The pill dispensing apparatus, through the main control unit and its remote communications ability, is capable of generating several different notifications. If a medication is not taken within the normal dispense window and the medication is deemed critical, the pill dispensing apparatus may transmit a missed notification message to one or more caregivers through any suitable communications link, including without limitation wired or wireless communication method via beepers, SMS, emails or a call to a monitoring service. The patient can also set the pill dispensing apparatus to vacation mode through the use of the touch screen when the patient is going to be away from the apparatus for an extended period of time. When operating in vacation mode, the apparatus will not dispense any pills, but will notify the patient, via a communication method such as described above, at the appropriate time to take the medication. The apparatus can also send a refill notification when one of the cartridges has, or nearly has, dispensed all of its pills.

The pill dispensing apparatus also maintains a log of all activity through the non-volatile memory of the main control unit. The log includes, but is not limited to, patient and caregiver information, medication schedules, actual medication dispenses, missed dispenses, loss of AC power, error conditions, etc. The information from the log can be formatted into a report upon request from an authorized caregiver and delivered to a remote device through the dispenser's remote communication channels, allowing authorized caregivers to see the real time status of the dispenser upon demand. Other reports may generated automatically upon completion of certain parameters and sent via the same remote communication channels.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

The invention claimed is:

1. An automatic pill dispensing apparatus for dispensing pills to a patent according to a prescription schedule comprising:
   a housing comprising an upwardly facing housing cover with a linear array of upwardly facing cartridge doors disposed under the housing cover, an information input/output display and a dispense button;
   a plurality of rotatable circular cartridges mounted on a centrally positioned, horizontally disposed primary shaft located inside the housing, each cartridge comprising a plurality of individual pill compartments, each cartridge having a plurality of fill positions wherein each pill compartment is selectively positionable beneath a fill opening defined by a cartridge door, and a plurality of dispense positions in which each pill compartment is selectively positionable and open at each dispense position;
   a pivoted dispense bar for closing each open pill compartment when the cartridge is in one of the dispense positions;
   a sweeping wire;
   a driver comprising a motor, at least one engageable clutch and complementary gears for rotating a cartridge to a successive dispense position;
   a control unit comprising
   (a) prescription dispense time input for each cartridge,
   (b) linking capability,
   (c) prescription dispense time sorting,
   (d) motor, clutch and gear control,
   (e) patient notification comprising audible alarm control and remote notification control;
   wherein, upon depression of the dispense button, the dispense bar pivots down which opens the pill compartment and the sweeping wire moves downward through the pill compartment and dislodges a pill into a dispense tray allowing patient access to the pill.

2. The automatic pill dispensing apparatus of claim 1 further configured to communicate with a remote access device.

3. The automatic pill dispensing apparatus of claim 1 further comprising a plurality of slits located on the periphery of each cartridge with each slit corresponding to each pill compartment, and an infrared emitter and receiver wherein the periphery of the cartridge is located between the emitter and the receiver, wherein the combination of the slits and the emitter and receiver are used to indicate the position of the cartridge.

4. The automatic pill dispensing apparatus of claim 1 further comprising a cartridge cover mounted on each cartridge to retain pills within the cartridge, wherein the cartridge cover remains stationary as the cartridge is rotated and the cartridge has an opening corresponding to the dispense bar.

5. The automatic pill dispensing apparatus of claim 4 wherein the cartridge cover further comprises a solid support axle which fits through a shaft in the center of each cartridge wherein the solid support axle provides a surface around which the cartridge rotates.

6. The automatic pill dispensing apparatus of claim 1 wherein the control unit further comprises a vacation notification.

7. The automatic pill dispensing apparatus of claim 1 further comprising a touch display.

8. The automatic pill dispensing apparatus of claim 1 wherein a compressible material is affixed to the dispense bar.

* * * * *